United States Patent [19]

Williams

[11] Patent Number: 5,574,034
[45] Date of Patent: Nov. 12, 1996

[54] PYRROLYL NAPHTHOPYRANS

[75] Inventor: Andrew C. Williams, Camberley, United Kingdom

[73] Assignee: Eli Lilly and Company, Indianapolis, Ind.

[21] Appl. No.: 463,838

[22] Filed: Jun. 5, 1995

Related U.S. Application Data

[62] Division of Ser. No. 215,344, Mar. 21, 1994, Pat. No. 5,514,699.

[30] Foreign Application Priority Data

Mar. 24, 1993 [GB] United Kingdom ............ 9306062

[51] Int. Cl.⁶ .................................. A61K 31/535
[52] U.S. Cl. .................. 514/232.8; 544/132; 544/139; 544/140; 544/150; 544/141; 544/126; 544/128; 544/124; 544/131; 546/279.1; 546/281.1; 546/273.4; 546/167; 546/194; 546/275.1; 546/276.4; 546/282.7; 546/89; 546/256; 546/268.4; 546/272.4; 546/272.7; 546/274.7; 546/275.4; 514/454; 548/525
[58] Field of Search ............... 549/389; 514/454, 514/232.8; 544/150; 548/525; 546/196, 268

[56] References Cited

U.S. PATENT DOCUMENTS

| | | | |
|---|---|---|---|
| 5,281,619 | 1/1994 | Dell et al. ........... | 514/454 |
| 5,284,868 | 2/1994 | Dell et al. ........... | 514/454 |
| 5,378,699 | 1/1995 | Brunaus et al. ...... | 514/312 |

FOREIGN PATENT DOCUMENTS

WO91/19707 12/1991 WIPO.

OTHER PUBLICATIONS

Elnagdi, et al., *Naturfoschung B*, 47(4), pp. 572–578 (1992).
Elagamey, et al. *Indian Journal of Chemistry*, 29B, 885–886 (1990).
Elagamey, et al., *Collection Czechoslovak Chem. Commun.*, 53(7), 1534–1538 (1988).
Otto, et al., *Monatshefte für Chemi*, 110, 115–119 (1979).
Otto, et al., *Monatshefte für Chemi*, 110, 249–256 (1979).
Otto, et al., *Arch. Pharm.*, 312(6), 548–550 (1979).
Abdel–Latif, *Indian Journal of Chemistry*, 29B, 664–666 (1990).
Sharanin, et al., *Zhurnal Organicheskoi Khimii*, 18, 9, 2003–2005 (1982).
Klokol, et al., *Zhurnal Organicheskoi Khimii*, 23, 2, 412–421 (1987).
Boxham, et al., *J. Chem. Soc. Perkin Trans. 1*, 24, 3055–3059 (1993).
Maybridge Chemical Company, Structure List No. 183, May 1989.
Maybridge Chemical Company, Exclusive Listing No. 1187/513684/13279, Nov. 6, 1987.
Maybridge Chemical Company, Exclusive Listing No. 288/513845/13684, Feb. 19, 1988.
Chemical Abstracts, *Heterocycles*, 85, 531 (1976).

*Primary Examiner*—Charles T. Jordan
*Assistant Examiner*—John R. Hardee
*Attorney, Agent, or Firm*—James P. Leeds; Janelle D. Strode; David E. Boone

[57] ABSTRACT

The invention provides pharmaceutical compounds of the formula:

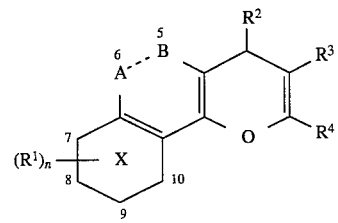

in which

A - - - B is $CH_2$—$CH_2$ or CH=CH;

X is a pyridine or benzene ring;

when X is pyridine n is 0;

when x is benzene n is 0, 1 or 2 and when A - - - B is $CH_2$—$CH_2$, $R^1$ is attached at any of the positions 7 to 10, and when A - - - B is CH=CH, $R^1$ is attached at any of the positions 5 to 10;

each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —$COOR^5$ where —$R^5$ is an ester group, —$COR^6$, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —$COOR^8$ where $R^8$ is an ester group, —$CONR^9R^{10}$ where $R^9$ and $R^{10}$ and each hydrogen or $C_{1-4}$ alkyl, or —$SO_2R^{11}$ where $R^{11}$ is $C_{1-4}$ alkyl, optionally substituted phenyl or optionally substituted phenyl-$C_{1-4}$ alkyl; and $R^4$ is 1-pyrrolyl, 1-imidazolyl or 1-pyrazolyl, said 1-pyrrolyl, 1-imidazolyl and 1-pyrazolyl being optionally substituted by one or two $C_{1-4}$ alkyl, carboxyl, hydroxy-$C_{1-4}$ alkyl or —CHO groups, or 1-(1,2,4-triazolyl), 1-(1,3,4-triazolyl) or 2-(1,2,3-triazolyl), said triazolyl groups being optionally substituted by a $C_{1-4}$ alkyl or $C_{1-4}$ perfluoroalkyl group, or 1-tetrazolyl optionally substituted by $C_{1-4}$ alkyl;

and salts thereof.

11 Claims, No Drawings

PYRROLYL NAPHTHOPYRANS

This application is a division of application Ser. No. 08/215,344, filed Mar. 21, 1994, now U.S. Pat. No. 5,514,699.

The invention relates to pharmaceutical compounds, their preparation and use.

The present invention comprises compounds of the formula:

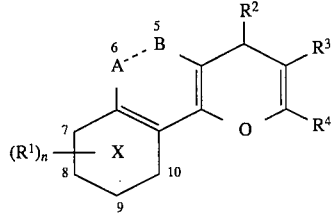

in which

A - - - B is $CH_2$—$CH_2$ or CH=CH;

X is a pyridine or benzene ring;

when X is pyridine n is 0;

when X is benzene n is 0, 1 or 2 and when A - - - B is $CH_2$—$CH_2$, $R^1$ is attached at any of the positions 7 to 10, and when A - - - B is CH=CH, $R^1$ is attached at any of the positions 5 to 10;

each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —$COOR^5$ where $R^5$ is an alkyl group, —$COR^6$, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —$COOR^8$ where $R^8$ is an alkyl group, —$CONR^9R^{10}$ where $R^9$ and $R^{10}$ are each hydrogen or $C_{1-4}$ alkyl, or —$SO_2R^{11}$ where $R^{11}$ is $C_{1-4}$ alkyl, optionally substituted phenyl or optionally substituted phenyl-$C_{1-4}$ alkyl; and $R^4$ is 1-pyrrolyl, 1-imidazolyl or 1-pyrazolyl, said 1-pyrrolyl, 1-imidazolyl and 1-pyrazolyl being optionally substituted by one or two $C_{1-4}$ alkyl, carboxyl, hydroxy-$C_{1-4}$ alkyl or —CHO groups, or 1-(1,2,4-triazolyl), 1-(1,3,4-triazolyl) or 2-(1,2,3-triazolyl), said triazolyl groups being optionally substituted by a $C_{1-4}$ alkyl or $C_{1-4}$ perfluoroalkyl group, or 1-tetrazolyl optionally substituted by $C_{1-4}$ alkyl;

and salts thereof.

In the above formula (I), A - - - B is $CH_2$—$CH_2$ or CH=CH, and compounds of the dihydronaphtho, naphtho, quinolinyl and dihydroquinolinyl type are encompassed. When X is pyridine, compounds of the following structures are covered:

Compounds in which the fused pyridine ring is as shown in (i), (ii) and (iii) are preferred.

A preferred group of compounds is of the formula:

in which n is 0, 1 or 2;

A - - - B is $CH_2$—$CH_2$ or CH=CH;

$R^1$ is attached at any of the positions 7 to 10 when A - - - B is CH—$CH_2$ or at any of the positions 5 to 10 when A - - - B is CH=CH; and $R^1$, $R^2$, $R^3$ and $R^4$ have the values defined above for formula (I); and salts thereof.

The compounds of the invention have been found to be active in tests which show their potential for treatment of immune diseases and diseases in which excess cell proliferation or enzyme release play a significant role.

In the above formulae, halo is, for example, fluoro, chloro or bromo and is especially chloro. A $C_{1-4}$ alkyl group includes, for example, methyl, ethyl, propyl and butyl, and is preferably methyl or ethyl. A $C_{1-4}$ alkoxy group is one such alkyl group linked through oxygen to an aryl nucleus, and a $C_{1-4}$ alkylthio is an alkyl group linked through sulphur. A hydroxyalkyl and hydroxyalkoxy are preferably of the formula $HO(CH_2)_x$— and $HO(CH_2)_xO$—, respectively, where x is 1 to 4.

A substituted phenyl group is substituted with one or more, preferably one or two substituents each selected from halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^{12}$ where $R^{12}$ is an alkyl group, —$CONR^{13}R^{14}$ or —$NR^{13}R^{14}$ where $R^{13}$ and $R^{14}$ are each hydrogen or $C_{1-4}$ alkyl. When $R^{12}$ is an alkyl group it is preferably $C_{1-4}$ alkyl, especially methyl or ethyl. Substituted naphthyl and heteroaryl groups may be similarly substituted. In addition substituted phenyl includes a phenyl group in which neighbouring atoms are substituted by —O(CH$_2$)$_m$O—, where m is 1, 2 or 3.

When n is 2 and there are two substituents on the nucleus they can be the same or different. It is preferred that the nucleus is unsubstituted.

When R$^1$ is —COOR$^5$, R$^5$ can be any alkyl group and is preferably C$_{1-4}$ alkyl, especially methyl or ethyl.

When R$^1$ is a nitrogen-containing heterocycle it is preferably selected from 2-pyridyl, 3-pyridyl, 4-pyridyl, 1-piperidino, 1-pyrrolidino and 4-morpholinyl.

Preferred examples of R$^1$ are carboxy, hydroxy, C$_{1-4}$ alkyl, C$_{1-4}$ alkoxy and —COOR$^5$.

When R$^2$ is heteroaryl it is preferably 2-thienyl, 3-thienyl, 2-pyridyl, 3-pyridyl, 4-pyridyl, 2-benzothienyl, 3-benzothienyl, 2-quinolinyl, 3- quinolinyl, 2-benzofuranyl, 3-benzofuranyl, 2-benzidimazolyl, 2-furanyl or 3-furanyl. A naphthyl group is attached at the 1- or 2-position. Such groups can be substituted at any of the available positions, but are preferably unsubstituted. Preferred values of R$^2$ are 2-thienyl, 3-thienyl, 3-pyridyl, 4-pyridyl, phenyl or substituted phenyl.

A particularly preferred value of R$^2$ is optionally substituted phenyl, preferably phenyl with a single substituent, especially nitro or trifluoromethyl.

The group R$^3$ is preferably nitrile. When R$^3$ is —COOR$^8$, R$^8$ can be any alkyl group and is preferably C$_{1-4}$ alkyl, especially methyl or ethyl.

The group R$^4$ is 1-pyrrolyl, 1-imidazolyl, 1-pyrazolyl, 1-(1,2,4-triazolyl, 1-(1,3,4-triazolyl), 2-(1,2,3-triazolyl) or 1-tetrazolyl. Such groups can be optionally substituted and preferred groups are represented as follows:

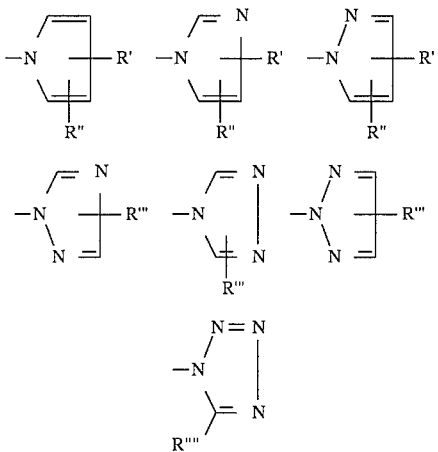

in which R' and R" are each hydrogen, C$_{1-4}$ alkyl, carboxyl, hydroxy-C$_{1-4}$ alkyl or —CHO, R''' is hydrogen, C$_{1-4}$ alkyl or C$_{1-4}$ perfluoroalkyl, and R'''' is hydrogen or C$_{1-4}$ alkyl.

The most preferred R$^4$ group is 1-pyrrolyl.

A particularly preferred group of compounds of formula (I) is as follows:

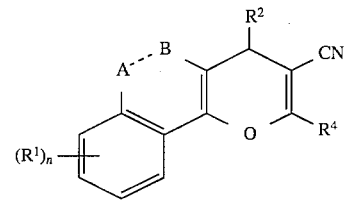

in which A - - - B and n are as defined above, R$^1$ is carboxy, hydroxy, C$_{1-4}$ alkyl, C$_{1-4}$ alkoxy or —COOR$^5$, R$^2$ is optionally substituted phenyl, and R$^4$ is optionally substituted 1-pyrrolyl; and salts thereof.

It will be appreciated that when for example, R$^1$ or R$^3$ is carboxy or R$^2$ is phenyl substituted by carboxy, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may served as intermediates in the purification of compounds or in the preparation of other, for example pharmaceutically-acceptable, acid addition salts, or are useful for identification, characterisation or purification.

In addition to salts formed with carboxy groups there can, of course, be esters formed with these same groups. Preferred esters are those derived from alcohols and especially C$_{1-4}$ alcohols such as, for example, the methyl or ethyl esters.

It will be appreciated that the compounds of the invention contain an asymmetric carbon atom at the 4-position which gives rise to enantiomers. The compounds are normally prepared as racemates and can conveniently be used as such, but individual enantiomers can be isolated by conventional techniques if so desired. Such racemates and individual enantiomers form part of the present invention.

The invention also comprises a process for producing a compound of the formula (I) above, which comprises:

1) reacting a compound of the formula:

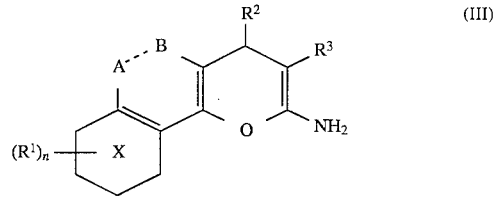

with a compound of the formula:

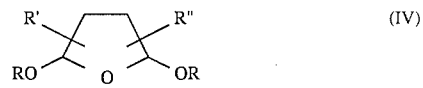

where RO— is a leaving group, preferably C$_{1-4}$ alkoxy, under acidic conditions, to give a compound of formula (I) in which R$^4$ is 1-pyrrolyl, 2) reacting a compound of formula (III) with a compound of the formula:

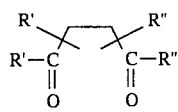

to give a compound of formula (I) in which $R^4$ is 1-pyrrolyl, 3) reacting a compound of the formula (III) with a compound of the formula:

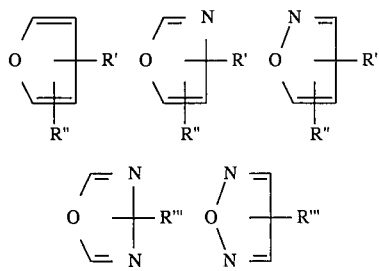

where the values of $R^1$, n, A - - - B, $R^2$, $R^3$, R', R" and R'" are as defined above, to give compounds in which $R^4$ is optionally substituted 1-pyrrolyl, 1-imidazolyl, 1-pyrazolyl, 1-(1,3,4-triazolyl) or 2-(1,2,3-triazolyl), 4) reacting a compound of the formula:

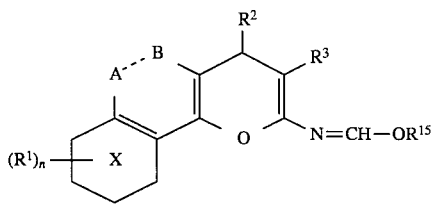

in which $R^{15}$ is a leaving group, with a formamidine of the formula $HN=CR'''—NH_2$, to give a compound in which $R^4$ is 1-(1,2,4-triazolyl), or 5) reacting a compound of the formula (III) with an azide to give a compound in which $R^4$ is 1-tetrazolyl.

As described in process variant (1), compounds of the invention in which $R^4$ is optionally substituted 1-pyrrolyl, can be prepared by reacting an amine of formula (III) with a tetrahydrofuran derivative of formula (IV) under acidic conditions, for example in the presence of acetic acid, and at an elevated temperature preferably between 50° and 100° C.

Reactants of formula (III) in which A - - - B is $CH_2—CH_2$ and X is benzene may be prepared by reaction of an arylidene tetralone of the formula:

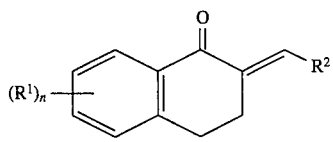

with malonitrile to give a compound in which $R^3$ is nitrile, or by converting a compound of the formula:

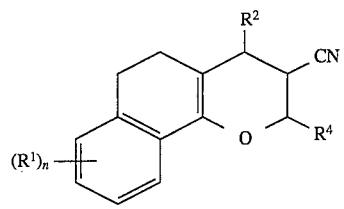

in which $R^4$ is a protected amino group, to give a compound in which $R^3$ is carboxy, $—COOR^8$ or $—CONR^9R^{10}$. Compounds of formula (VI) are known or can be easily synthesised by known methods. For example, they can be prepared from compounds of formula:

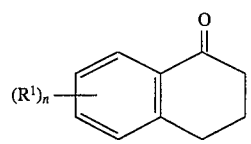

by reaction with an aldehyde of formula $R^2CHO$ in the presence of an acid catalyst such as, for example, toluene sulphonic acid, or when $R^2$ is an acid sensitive group such as pyridyl, under basic conditions, with, for example, potassium hydroxide and ethanol.

Reactants of formula (III) in which A - - - B is CH=CH and X is benzene may be prepared by reacting a compound of the formula:

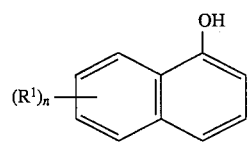

with a compound of the formula:

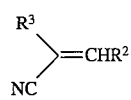

which can in its turn be prepared by reacting the appropriate nitrile of formula $R^3CH_2CN$ with an aldehyde of formula $R^2CHO$.

The compounds of formula (III) in which X is pyridine can be prepared by similar methods starting from the appropriate hydroxyquinolines or hydroxyisoquinolines.

With regard to process variant (2), the reaction is preferably carried out at a temperature of from 0° C. to 100° C., in an organic solvent such as for example toluene, in the presence of an acidic catalyst such as acetic or p-toluene sulphonic acid. Compounds of formula (V) are known or readily prepared by conventional means.

As described in process variant (3), compounds of the invention can be prepared by reaction of the amine of formula (III) with a suitable oxygen-containing heterocycle. The reaction is preferably carried out at a temperature of from 0° C. to 150° C., in an organic solvent such as, for example, toluene or dimethylformamide. Reactions of this type are described in Comprehensive Heterocyclic Chemistry Volume 5 page 156 et seq., Pergamon Press Ltd., 1984.

With regard to process variant (4), the reaction is preferably carried out at a temperature of from 0° C. to 100° C., in an organic solvent such as, for example, dimethylformamide. The formamidine reactant can be prepared by conventional means, and the compound of formula (V) by reaction of a compound of formula (III) with a reagent such as triethyl orthoformate to give a compound of formula (V) in which the leaving group, $R^{15}$, is ethyl.

With regard to process variant (5), the reaction is preferably carried out at a temperature of from 0° C. to 100° C., in an organic solvent such as, for example, dimethylformamide. The azide employed is preferably an alkali metal azide, especially sodium azide.

As mentioned above, the compounds have pharmaceutical activity. They have an antiproliferative effect on cell division, and are thus indicated for use in the treatment of diseases where excess cell proliferation or enzyme release is an important aspect of the pathology.

For example, the compounds of the invention inhibit the natural proliferation of 3T3 fibroblasts at $IC_{50}$ concentrations of below 20µ molar.

Furthermore, the compounds have been shown to modify the immune response by inhibiting concanavalin A-induced T-cell proliferation in the test described by Lacombe P. et al., FEBS, 3048, 191, 227–230. In general the compounds of the invention have an $IC_{50}$ value in this test of below 10 µM.

The compounds also inhibit cell proliferation in an NS-1 murine B-lymphoma line, and phorbol ester-stimulated plasminogen activator synthesis in bovine retinal capillary endothelial cells.

Inhibition of macrophage-conditioned medium induced neutral protease release in chondrocytes has also been observed in the test described by K. Deshmukh-Phadke, M. Lawrence and S. Nanda, Biochem. Biophys. Res. Commun., 1978, 85, 490–496.

Such properties show that the compounds have potential in the treatment of a wide range of diseases such as, for example, rheumatoid arthritis, atherosclerosis, cirrhosis, fibrosis and cancer, and for the treatment of auto-immune diseases such as, for example, systemic lupus, and in the prevention of graft rejection. They are also indicated for the treatment of osteoarthritis and diabetic complications.

Furthermore, compounds of the invention have been shown to inhibit vascular smooth cell proliferation. This has been demonstrated by using cultured smooth cells derived from rabbit aortae, proliferation being determined by the measurement of DNA synthesis. Cells are obtained by explant method as described in Ross, J. of Cell Bio. 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 µg ml streptomycin, 1 µC/ml $^3$H-thymidine, 20 ng/ml platelet-derived growth factory and varying concentrations of the compounds. Stock solution of compounds is prepared in dimethyl sulphoxide and then diluted to appropriate concentration (0.1–10 µg/ml) in the above assay medium. Cells are then incubated at 37° C. for 24 hours under 5% $CO_2$/95% air. At the end of 24 hours, the cells are fixed in methanol. $^3$H thymidine incorporation in DNA was then determined by scintillation counting as described in Bonin et al., Exp. Cell Res. 181: 475–482 (1989).

Inhibition of smooth muscle cell proliferation by the compounds of the invention is further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 µg/ml streptomycin. After 24 hours, the cells are attached, the medium is replaced with DMEM containing 2% platelet poor plasma, 2 mM L-glutamine, 100 U/ml penicillin, 100 µg/ml streptomycin, 40 ng/ml platelet-derived growth factor and indicated concentrations of the compounds. Cells are allowed to grow for four days. Cells are treated with trypsin and number of cells in each cultures is determined by counting using a ZM-Coulter counter.

Activity in the above tests indicates that the compounds of the invention are of potential in the treatment of restenosis, which is characterised by the migration and proliferation of smooth muscle cells in response to injury.

The invention also includes a pharmaceutical composition comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propylhydroxybenzoate, talc magnesium stearate and mineral oil. The compositions of the injection may, as it well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

3-Nitrobenzaldehyde (40 g) and malonitrile (17.6 g) were dissolved in ethanol (200 ml). The solution was heated to reflux temperature then piperidine (0.5 ml) was added. Once the vigorous reaction had subsided heating was recommenced and maintained at reflux temperature for 30 minutes. The solution was allowed to cool to room temperature, whereupon a pale, creamy yellow precipitate of 3-nitrobenzylidenemalonitrile was thrown down. This was filtered off, washed with ether and dried, m.p. 108° C.

The following compounds were prepared in a similar manner:
3,4-(Methylenedioxy)benzylidenemalonitrile, m.p. 201°–202° C.
3-(Trifluoromethyl)benzylidenemalonitrile, m.p. 81° C.
3,4-(Dimethoxy)benzylidenemalonitrile, m.p. 137° C.
α-Methanesulphonyl-3-nitrocinnamonitrile, m.p. 157° C.
3,4-(Dichloro)benzylidenemalonitrile, m.p. 154° C.
1-(3-Pyridyl)methylidenemalonitrile, m.p. 89° C.
3-Methoxybenzylidenemalonitrile, m.p. 102° C.
3-Carbomethoxybenzylidenemalonitrile, m.p. 125° C.

EXAMPLE 2

1-Naphthol (2.2 g) was stirred in ethanol (20 ml) at ambient temperature. To this suspension was 3-nitrobenzylidenemalonitrile (3 g) and piperidine (1.5 ml). All solids dissolved, heat was evolved, and once the initial vigorous reaction had subsided heating was commenced and maintained at reflux temperature for 15 minutes. Crystals of 2-amino-4-(3-nitrophenyl)-4H-naphtho[1,2-b]pyran-3-carbonitrile came out of solution and after the solution had cooled back to ambient temperature they were collected by filtration, washed with ether and dried, m.p. 214.5°–216° C.

The following compounds were prepared in a similar manner:
2-Amino-4-(3,4-methylenedioxyphenyl)-4H-naphtho[1,2-b]pyran-3-carbonitrile, m.p. 249°–252° C.
[(2-Amino)-4-(3-nitrophenyl)-4H-naphtho[1,2-b]pyran-3-yl]methyl sulphone, m.p. 173° C.
2-Amino-4-(3,4-dimethoxyphenyl)-4H-naphtho[1,2-b]pyran-3-carbonitrile, m.p. 207°–209.5° C.
2-Amino-4-(3,4-dichlorophenyl)-4H-naphtho[1,2-b]pyran-3-carbonitrile, m.p. 247°–249° C.
2-Amino-4-(3-methoxyphenyl)-4H-naphtho[1,2-b]pyran-3-carbonitrile, m.p. 139°–142.5° C.
2-Amino-4-(3-pyridyl)-4H-naphtho[1,2-b]pyran-3-carbonitrile, m.p. 205°–207° C.
Methyl 3-(2-amino-3-cyano-4H-naphtho[1,2-b]pyran-4-yl)benzoate, m.p. 235°–236° C.

EXAMPLE 3

1) A mixture of 3,4-dihydro-1(2H)-naphthalenone (21.9 g), 3-nitrobenzaldehyde (22.6 g) and p-toluenesulphonic acid monohydrate (50 mg) in toluene (250 ml) was stirred at reflux with separation of water for 4.5 hours. The brown solution was allowed to cool overnight, the resultant orange-yellow solid filtered off, washed with toluene and dried in vacuo to give 2-(3-nitrobenzylidene)-3,4-dihydro-1(2H)-naphthalenone as yellow needles.

2-[1-(3-Pyridyl)methylidene]-3,4-dihydro-1(2H)-naphthalenone was prepared according to the procedure of J. Sam and K. Aparajithan, J. Pharm. Sci., 1967, 56(5), 644.

The following compounds were prepared by methods similar to the above:
2-(3,4-Dichlorobenzylidene)-3,4-dihydro-1(2H)-naphthalenone.
2-(3,4-Dimethoxybenzylidene)-3,4-dihydro-1(2H)-naphthalenone.
3,4 Methylenedioxybenzylidene-3,4-dihydro-1(2H)-naphthalenone.
7-Methoxy-2-(2-thienylidene)-3,4-dihydro-1(2H)-naphthalenone.

EXAMPLE 4

A stirred suspension of 2-[1-(3-Pyridyl)methylidene]-3,4-dihydro-1(2H)-naphthalenone (8 g) and malonitrile (2.5 g) in ethanol (50 ml) was heated to reflux temperature, then piperidine (3.5 ml) was added and the solution maintained at reflux for one hour. It was then allowed to cool to ambient temperature whereupon a white solid was precipitated, which was separated by filtration, washed with ether and dried in vacuo, yielding 2-amino-4-(3-pyridyl)-4H-5,6-dihydronaphtho[1,2-b]pyran-3-carbonitrile as a white powder. m.p. 165°–166° C.

The following compounds were prepared by the above procedure:
2-Amino-4-(3-nitrophenyl)-4H-5,6-dihydronaphtho[1,2-b]pyran-3-carbonitrile, m.p. 175°–176° C.
2-Amino-4-(3,4-dimethoxyphenyl)-4H-5,6-dihydronaphtho[1,2-b]pyran-3-carbonitrile, m.p. 190°–191° C.
2-Amino-4-(3,4-methylenedioxyphenyl)-4H-5,6-dihydronaphtho[1,2-b]pyran-3-carbonitrile, m.p. 250°–252° C.
2-Amino-4-(3-dichlorophenyl)-4H-5,6-dihydronaphtho[1,2-b]pyran-3-carbonitrile, m.p. 215°–216° C.
2-Amino-9-methoxy-4-(2-thienyl)-4H-5,6-dihydronaphtho[1,2-b]pyran-3-carbonitrile, m.p. 198°–199° C.

EXAMPLE 5

Dihydroxynaphthalene-2-carboxylic acid (25 g) was dissolved in 500 ml ethanol. To this was added 25 ml thionyl chloride. The solution was heated under reflux for 4 hours. Then the solvent was removed under reduced pressure and the resulting solid dissolved in 500 ml ethyl acetate. The organic phase was washed with aqueous potassium carbonate/potassium acetate (1M in each) (3×350 ml). The organic phase was dried over magnesium sulphate then the solvent removed under reduced pressure to yield ethyl 3,5-dihydroxynaphthalene-2-carboxylate as a yellow solid.

EXAMPLE 6

To a solution of ethyl 3,5-dihydroxynaphthalene-2-carboxylate (4.5 g) in ethanol (40 ml) was added 3-nitrobenzylidenemalonitrile (3.9 g) and piperidine (1.95 ml). The mixture was heated under reflux for 15 minutes whereupon a yellow precipitate was observed to form. The mixture was allowed to cool to room temperature, diluted with ether (100 ml) and the solid filtered off to yield ethyl 2-amino-3-cyano-9-hydroxy-4-(3-nitrophenyl)-4H-naphtho[1,2-b]pyran-8-carboxylate as a yellow powder, m.p. 260°–261° C. (dec.)

The following compounds were prepared in a similar manner.
Ethyl 2-amino-3-cyano-9-hydroxy-4-(3,4-methylenedioxyphenyl)-4H-naphtho[1,2-b]pyran-8-carboxylate, m.p. 262°–263° C. (dec.)
Ethyl 2-amino-3-cyano-9-hydroxy-4-(3,4-dimethoxyphenyl)-4H-naphtho[1,2-b]pyran-8-carboxylate, m.p. 222°–223° C.
Ethyl 2-amino-3-cyano-9-hydroxy-4-(3,4-dichlorophenyl)-4H-naphtho[1,2-b]pyran-8-carboxylate, m.p. 261°–262° C. (dec.)

Ethyl 2-amino-3-cyano-9-hydroxy-4-(3-pyridyl)-4H-naphtho[1,2-b]pyran-8-carboxylate, m.p. 259°–261° C. (dec.)

Ethyl 2-amino-3-cyano-9-hydroxy-4-(3-methoxyphenyl)-4H-naphtho[1,2-b]pyran-8-carboxylate, m.p. 212°–214° C.

Ethyl 2-amino-3-cyano-9-hydroxy-4-(3-trifluoromethylphenyl)-4H-naphtho[1,2-b]pyran-8-carboxylate, m.p. 234°–236° C.

EXAMPLE 7

3-Carbomethoxybenzylidenemalonitrile (3.08 g) and 8-hydroxyquinoline (2.11 g) were suspended in ethanol (15 ml). Piperidine (4 drops) was added and the mixture warmed to just below reflux temperature for 30 minutes. The resulting dark solution was cooled in a refrigerator for one hour and the crystalline precipitate filtered off, washed with ether and dried to yield methyl 3-(2-amino-3-cyano-4H-pyrano[3,2-h]quinolin-4-yl)benzoate, m.p. 208°–210° C.

2-Amino-4-(3-nitrophenyl)-4H-pyrano[3,2-h]quinoline-3-carbonitrile, m.p. 198°–200° C., was prepared in a similar manner.

EXAMPLE 8

3-Carbomethoxybenzylidenemalonitrile (3.13 g) and 5-hydroxyquinoline (2.14 g) were suspended in ethanol (12 ml) and heated to produce a dark solution. Piperidine (2 drops) was added and the mixture heated to just below reflux temperature for 45 minutes. The flask was cooled to room temperature, then solvent removed under reduced pressure to yield a red oil. This was triturated with ethanol (10 ml) and ether (50 ml), the resulting red solid removed by filtration and the filtrate evaporated to yield an orange-brown solid. This was triturated with ether, to yield methyl 3-(2-amino-3-cyano-4H-pyrano[2,3-f]quinolin-4-yl)benzoate as an orange solid, m.p. 203°–206° C.

EXAMPLE 9

3-Carbomethoxybenzylidenemalonitrile (3.01 g) and 5-hydroxyisoquinoline (2.06 g) were suspended in ethanol (14 ml). Piperidine (4 drops) was added and the mixture heated to just below reflux temperature for 2 hours, then cooled to room temperature. Ether (30 ml) was added, the solid precipitate collected by filtration, washed with ether (2×20 ml) and dried to yield methyl 3-(2-amino-3-cyano-4H-pyran-[2,3-f]isoquinolin-4-yl)benzoate as an off-white solid, m.p. 229°–230° C.

2-Amino-4-(3-nitrophenyl)-4H-pyrano[2,3-f]isoquinoline-3-carbonitrile, m.p. 239°–243° C. was prepared in a similar manner.

EXAMPLE 10

2-Amino-4-(3-nitrophenyl)-4H-naphtho[1,2-b]pyran-3-carbonitrile (1 g), was dissolved in glacial acetic acid (25 ml). To this solution was added 2,5-dimethoxytetrahydrofuran (0.42 ml). The solution was heated to reflux temperature for 30 minutes, allowed to cool back to ambient temperature, then poured into brine (200 ml). Ethyl acetate (100 ml) was added, the aqueous and organic phases separated, and the aqueous phase extracted a further two times with ethyl acetate (2×100 ml). The combined organic extracts were washed twice with 20% aqueous potassium carbonate (2×200 ml), then dried over magnesium sulphate. The drying agent was removed by filtration and the solvents removed under reduce pressure to give crude 4-(3-nitrophenyl)-2-(1-pyrrolyl)-4H-naphtho[1,2-b]pyran-3-carbonitrile as a yellow brown foam. This was purified by flash chromatography, eluting with 3:1 to 1:1 hexane/ether to give the product as a creamy yellow solid, m.p. 197.5°–198.5° C.

The following were prepared in a similar manner.

4-(3,4-Methylenedioxyphenyl)-2-(1-pyrrolyl)-4H-naphtho[1,2-b]pyran-3-carbonitrile, m.p. 176° C.

4-(3,4-Dimethoxyphenyl)-2-(1-pyrrolyl)-4H-naphtho[1,2-b]pyran-3-carbonitrile, m.p. 184°–185° C.

4-(3,4-Dichlorophenyl)-2-(1-pyrrolyl)-4H-naphtho[1,2-b]pyran-3-carbonitrile, m.p. 153°–154° C.

4-(3-Pyridyl)-2-(1-pyrrolyl)-4H-naphtho[1,2-b]pyran-3-carbonitrile, m.p. 188°–189° C.

4-(3,4-Dimethoxyphenyl)-2-(1-pyrrolyl)-4H-5,6-dihydronaphtho[1,2-b]pyran-3-carbonitrile, m.p. 162° C.

4-(3,4-Dichlorophenyl)-2-(1-pyrrolyl)-4H-5,6-dihydronaphtho[1,2-b]pyran- 3-carbonitrile, m.p. 160° C.

4-(3-Nitrophenyl)-2-(1-pyrrolyl)-4H-5,6-dihydronaphtho[1,2-b]pyran-3-carbonitrile, m.p. 183° C.

4-(3-Pyridyl)-2-(1-pyrrolyl)-4H-5,6-dihydronaphtho[1,2-b]pyran-3-carbonitrile, m.p. 163°–164° C.

9-Methoxy-2-(1-pyrrolyl)-4-(2-thienyl)-4H-5,6-dihydronaphtho[1,2-b]pyran-3-carbonitrile, m.p. 171° C.

Methyl 3-[3-cyano-2-(1-pyrrolyl)-4H-naphtho[1,2-b]pyran-4-yl]benzoate, m.p. 194°–195° C.

4-(3-Methoxyphenyl)-2-(1-pyrrolyl)-4H-naphtho[1,2-b]pyran-3-carbonitrile, m.p. 142°–143° C.

4-(3,4-Methylenedioxyphenyl)-2-(1-pyrrolyl)-4H-5,6-dihydronaphtho[1,2-b]pyran-3-carbonitrile, m.p. 163°–165° C.

Methyl 3-[3-cyano-2-(1-pyrrolyl)-4H-pyrano[3,2-h]quinolin-4-yl]benzoate, m.p. 202°–203° C.

Methyl 3-[3-cyano-2-(1-pyrrolyl)-4H-pyrano[2,3-f]isoquinolin-4-yl]benzoate, m.p. 164°–166° C.

Methyl 3-[3-cyano-2-(1-pyrrolyl)-4H-pyrano[2,3-f]quinolin-4-yl]benzoate, m.p. 200°–201° C.

4-(3-Nitrophenyl-2-(1-pyrrolyl)-4H-pyrano[2,3-f]isoquinoline-3-carbonitrile, m.p. 225°–227° C.

Ethyl 3-cyano-9-hydroxy-4-(3-pyridyl)-2-(1-pyrrolyl)-4H-naphtho[1,2-b]pyran-8-carboxylate, m.p. 232° C. (dec.)

Ethyl 3-cyano-4-(3,4-dichlorophenyl)-9-hydroxy-2-(1-pyrrolyl)-4H-naphtho[1,2-b]pyran-8-carboxylate, m.p. 240°–241° C.

Ethyl 3-cyano-4-(3,4-dimethoxyphenyl)-9-hydroxy-2-(1-pyrrolyl)-4H-naphtho[1,2-b]pyran-8-carboxylate, m.p. 235° C.

Ethyl 3-cyano-9-hydroxy-4(3,4-methylenedioxyphenyl)-2-(1-pyrrolyl)-4H-naphtho[1,2-b]pyran-8-carboxylate, m.p. 251°–252° C.

Ethyl 3-cyano-9-hydroxy-4-(3-nitrophenyl)-2-(1-pyrrolyl)-4H-naphtho[1,2-b]pyran-8-carboxylate, m.p. 233° C.

4-(3-Nitrophenyl)-2-(1-pyrrolyl)-4H-pyrano[3,2-h]quinoline-3-carbonitrile, m.p. 234°–235° C.

[4-(3-Nitrophenyl)-2-(1-pyrrolyl)-4H-naphtho[1,2-b]pyran-3-yl]methyl sulphone, m.p. 237.5°–239° C.

EXAMPLE 11

Ethyl 3-cyano-9-hydroxy-4-(3-nitrophenyl)-2-(1-pyrrolyl)-4H-naphtho[1,2-b]pyran-8-carboxylate (4 g) was dissolved in dry DMF (50 ml). Solid potassium carbonate (2.3 g) and methyl iodide (1.05 ml) were added and the mixture stirred at room temperature for 16 hours. The solution was poured into water (400 ml) and extracted with ethyl acetate (4×200 ml). The combined organic extracts were washed with water (3×250 ml), dried over magnesium suphate, then solvent was removed under reduced pressure to yield a brown solid. This was triturated with ether (10 ml), the solid collected by filtration and dried to yield ethyl 3-cyano-9-methoxy-4-(3-nitrophenyl)-2-(1-pyrrolyl)-4H-naphtho[1,2-b]pyran-8-carboxylate as a dark yellow solid, m.p. 190°–191° C.

Ethyl 3-cyano-9-ethoxy-4-(3-nitrophenyl)-2-(1-pyrrolyl)-4H-naphtho[1,2-b]pyran-8-carboxylate, m.p. 202°–203° C. was prepared in a similar manner.

EXAMPLE 12

Ethyl 3-cyano-9-hydroxy-4-(3-nitrophenyl)-2-(1-pyrrolyl)-4H-naphtho[1,2-b]pyran-8-carboxylate (1.91 g) was dissolved in THF (10 ml). Water (1 ml) and lithium hydroxide monohydrate (180 mg) were added and the solution stirred at room temperature for 45 minutes. A further quantity of lithium hydroxide (180 mg) was added and the solution heated under reflux for one hour. The solution was poured into water (100 ml) and glacial acetic acid (50 ml) added. Solid sodium chloride was added until no more would dissolved, then the mixture extracted with ethyl acetate (3×200 ml). The combined organic extracts were dried over magnesium sulphate, then solvent removed under reduced pressure to give a brown-yellow solid. This was triturated with ether (10 ml), the solid collected by filtration and dried to yield 3-cyano-9-hydroxy-4-(3-nitrophenyl)-2-(1-pyrrolyl)-4H-naphtho[1,2-b]pyran-8-carboxylic acid, m.p. >230° C.

EXAMPLE 13

2-Amino-4-(3-nitrophenyl)-4H-naphtho[1,2-b]pyran-3-carbonitrile (1 g), was dissolved in glacial acetic acid (25 ml). To this solution was added 2,5-dimethoxytetrahydrofuran (0.42 ml). The solution was heated to reflux temperature for 30 minutes, allowed to cool back to ambient temperature, then poured into brine (200 ml). Ethyl acetate (100 ml) was added, the aqueous and organic phases separated, and the aqueous phase extracted a further two times with ethyl acetate (2×100 ml). The combined organic extracts were washed twice with 20% aqueous potassium carbonate (2×200 ml), then dried over magnesium sulphate. The drying agent was removed by filtration and the solvents removed under reduced pressure to give crude 4-(3-nitrophenyl)-2-(1-pyrrolyl)-4H-naphtho[1,2-b]pyran-3-carbonitrile as a yellow brown foam. This was purified by flash chromatography, eluting with 3:1 to 1:1 hexane/ether to give the product as a creamy yellow solid, m.p. 197.5°–198.5° C.

The following compounds were prepared in a similar manner.

4-(3,4-Methylenedioxyphenyl)-2-(1-pyrrolyl)-4H-naphtho[1,2-b]pyran-3-carbonitrile, m.p. 176° C.

4-(3,4-Dimethoxyphenyl)-2-(1-pyrrolyl)-4H-naphtho[1,2-b]pyran-3-carbonitrile, m.p. 184°–185° C.

4-(3,4-Dichlorphenyl)-2-(1-pyrrolyl)-4H-naphtho[1,2-b]pyran-3-carbonitrile, m.p. 153°–154° C.

4-(3-Pyridyl)-2-(1-pyrrolyl)-4H-naphtho[1,2-b]pyran-3-carbonitrile.

4-(3,4-Dimethoxyphenyl)-2-(1-pyrrolyl)-4H-5,6-dihydronaphtho[1,2-b]pyran-3-carbonitrile.

4-(3,4-Dichlorophenyl)-2-(1-pyrrolyl)-4H-5,6-dihydronaphtho[1,2-p]pyran-3-carbonitrile.

4-(3-Nitrophenyl)-2-(1-pyrrolyl)-4H-5,6-dihydronaphtho[1,2-b]pyran-3-carbonitrile.

4-(3-Pyridyl)-2-(1-pyrrolyl)-4H-5,6-dihydronaphtho[1,2-b]pyran-3-carbonitrile.

9-Methoxy-2-(1-pyrrolyl)-4-(2-thienyl)-4H-5,6-dihydronaphtho[1,2-b]pyran-3-carbonitrile.

EXAMPLE 14

Soft gelatin capsule

Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 15

Hard gelatin capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 16

Tablets each containing 10 mg of active ingredient are made up as follows:

| Active ingredient | 10 mg |
|---|---|
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

EXAMPLE 17

Capsules each containing 20 mg of medicament are made as follows:

| Active ingredient | 20 mg |
|---|---|
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 18

The concanavalin A response of rat spleen cells was used as a primary in vitro assay to determine the activity of the compounds of the invention. Many methods for the determination of concavalin A response are described in the literature. The method employed was similar to that described by Lacombe P. et al., FEBS 3048 191, 227–230. We used $2\times10^5$ cells per culture well, and concanavalin A was employed at 1 μg/ml. 2-Mercaptoethanol was a requirement ($2\times10M^{-5}$) and 0.25 μCi of tritiated thymidine was added six hours before cell harvesting.

For example, the following compounds have an $IC_{50}$ in the range of from 0.01 to 0.7 μM:

3-Cyano-4-(3-nitrophenyl)-2-(1-pyrrolyl)-4H-naphtho[1,2-b]pyran.

4-(3,4-Dimethoxyphenyl)-2-(1-pyrrolyl)-4H-naphtho[1,2-b]pyran-3-carbonitrile.

4-(3-Pyridyl)-2-(1-pyrrolyl)-4H-5,6-dihydronaphtho[1,2-b]pyran-3-carbonitrile.

4-(3-Pyridyl)-2-(1-pyrrolyl)-4H-naphtho[1,2-b]pyran-3-carbonitrile.

4-(3-Nitrophenyl)-2-(1-pyrrolyl)-4H-pyrano[3,2-h]quinoline-3-carbonitrile.

4-(2-Thienyl)-2-(1-pyrrolyl)-9-methoxy-4H-5,6-dihydronaphtho[1,2-b]pyran-3-carbonitrile.

I claim:

1. A compound of the formula:

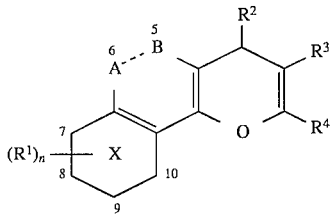

in which

A - - - B is $CH_2$—$CH_2$ or CH=CH;

X is a benzene ring;

n is 0, 1 or 2 and when A - - - B is $CH_2$—$CH_2$, $R^1$ is attached at any of the positions 7 to 10, and when A - - - B is CH=CH, $R^1$ is attached at any of the positions 5 to 10;

each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, pyridyl, piperidino, pyrrolidino, morpholino, nitro, trifluoromethoxy, —$COOR^5$ where $R^5$ is an alkyl group, —$COR^6$, —$CONR^6R^7$ or —$NR^6R^7$ where $R^6$ and $R^7$ are each hydrogen or $C_{1-4}$ alkyl;

$R^2$ is phenyl substituted by —$O(CH_2)_mO$— where m is 1, 2, or 3;

$R^3$ is nitrile, carboxy, —$COOR^8$ where $R^8$ is an alkyl group, or —$SO_2R^{11}$ where $R^{11}$ is $C_{1-4}$ alkyl; and $R^4$ is 1-pyrrolyl;

and salts thereof.

2. A compound according to claim 1 in which $R^2$ is 3,4-methylenedioxyphenyl, $R^3$ is nitrile and $R^4$ is 1-pyrrolyl.

3. The compound according to claim 2 in which A - - - B is $CH_2$—$CH_2$.

4. The compound according to claim 2 in which A - - - B is CH=CH.

5. The compound according to claim 2 which is 4-(3,4-methylenedioxyphenyl)-2-(1-pyrrolyl)-4H-naptho[1,2-b]pyran-3-carbonitrile.

6. The compound according to claim 2 which is 4-(3,4-methylenedioxyphenyl)-2-(1-pyrrolyl)-4H-5,6-dihydronpatho[1,2-b]pyran-3-carbonitrile.

7. The compound according to claim 2 which is ethyl 3-cyano-9-hydroxy-4-(3,4-methylenedioxyphenyl)-2-(1-pyrrolyl)-4H-naptho[1,2-b]pyran-8-carboxylate.

8. A pharmaceutical formulation comprising a compound according to claim 1 or a pharmaceutically acceptable salt thereof, together with a pharmaceutically acceptable carrier or diluent therefor.

9. A method of treating an immune disease or a disease in which excess cell proliferation or enzyme release occur, which comprises administering to a patient in need of treatment a therapeutic dosage of a compound as defined in claim 8.

10. A method of treating restenosis, which comprises administering to a patient in need of treatment a therapeutic dosage of a compound as defined in claim 5.

11. A method of inhibiting vascular smooth muscle cells, which comprises administering to a patient in need of treatment a therapeutic dosage of a compound as defined in claim 8.

* * * * *

UNITED STATES PATENT AND TRADEMARK OFFICE
CERTIFICATE OF CORRECTION

PATENT NO. : 5,574,034
DATED : November 12, 1996
INVENTOR(S) : Andrew C. Williams It is certified that error appears in the above-identified patent and that said Letters Patent is hereby corrected as shown below:

On the title page, item

[56] References Cited; US Patent Document; 5,378, 699; delete "Brunaus" add --Brunavs--.

Signed and Sealed this

Second Day of May, 2000

Attest:

Q. TODD DICKINSON

Attesting Officer

Director of Patents and Trademarks